(12) United States Patent
Bierbaum et al.

(10) Patent No.: US 9,743,998 B2
(45) Date of Patent: Aug. 29, 2017

(54) DENTAL PREPARATION INSTRUMENT HAVING A TOOL THAT ROTATES IN AN ALTERNATELY REVERSIBLE MANNER

(71) Applicant: DENTSPLY SIRONA Inc., York, PA (US)

(72) Inventors: Thomas Bierbaum, Bensheim (DE); Adelbert Lauffer, Reutlingen (DE)

(73) Assignee: DENTSPly Sirona Inc., York, PA (US)

( * ) Notice: Subject to any disclaimer, the term of this patent is extended or adjusted under 35 U.S.C. 154(b) by 77 days.

(21) Appl. No.: 14/431,438

(22) PCT Filed: Sep. 30, 2013

(86) PCT No.: PCT/EP2013/070312
§ 371 (c)(1),
(2) Date: Mar. 26, 2015

(87) PCT Pub. No.: WO2014/049167
PCT Pub. Date: Apr. 3, 2014

(65) Prior Publication Data
US 2015/0366632 A1      Dec. 24, 2015

(30) Foreign Application Priority Data
Sep. 28, 2012   (DE) .................. 10 2012 217 851

(51) Int. Cl.
*A61C 1/06*          (2006.01)
*A61C 1/18*          (2006.01)
(Continued)

(52) U.S. Cl.
CPC ............... *A61C 1/186* (2013.01); *A61C 1/02* (2013.01); *A61C 1/12* (2013.01); *A61C 1/185* (2013.01); *A61C 1/06* (2013.01); *A61C 5/40* (2017.02)

(58) Field of Classification Search
CPC ........... A61C 1/148; A61C 1/186; A61C 1/02; A61C 1/12; A61C 3/02; A61C 5/023
(Continued)

(56) References Cited

U.S. PATENT DOCUMENTS 3,578,745 A    5/1971   Garnier
4,718,851 A    1/1988   Kuhn
(Continued)

FOREIGN PATENT DOCUMENTS

DE    1993113 U    9/1968
EP    1196109 B1   11/2006
(Continued)

OTHER PUBLICATIONS

International Search Report mailed Jan. 30, 2014, in International Application No. PCT/EP2013/070312.
(Continued)

*Primary Examiner* — Ralph Lewis
(74) *Attorney, Agent, or Firm* — Douglas J. Hura; David A. Zdurne; Leana Levin

(57) ABSTRACT

The invention relates to a dental preparation instrument that includes a tool that rotates in an alternately reversible manner. The preparation instrument has a drive for the tool. The drive provides a continuous fully rotational motion, and a gearing is arranged before the tool. Said gearing converts the continuous fully rotational motion of the drive into an alternately reversing rotational motion, which is continuous as viewed over several reversals.

7 Claims, 5 Drawing Sheets

(51) Int. Cl.
    *A61C 1/12* (2006.01)
    *A61C 1/02* (2006.01)
    *A61C 5/40* (2017.01)

(58) Field of Classification Search
    USPC .................. 433/105, 118, 122, 123, 124
    See application file for complete search history.

(56) References Cited

U.S. PATENT DOCUMENTS

| | | |
|---|---|---|
| 6,293,795 B1 | 9/2001 | Johnson |
| 8,714,978 B2 | 5/2014 | Borgschulte |
| 2014/0318287 A1* | 10/2014 | Eder .................. F16H 19/08 74/88 |

FOREIGN PATENT DOCUMENTS

| | | |
|---|---|---|
| EP | 2438884 A1 | 4/2012 |
| WO | 82/03760 A1 | 11/1982 |

OTHER PUBLICATIONS

German Office Action mailed May 22, 2013 in German Patent Application No. 10 2012 217 851.1.
International Preliminary Report on Patentability dated Mar. 31, 2015 in PCT/EP2013/070312.

* cited by examiner

DENTAL PREPARATION INSTRUMENT HAVING A TOOL THAT ROTATES IN AN ALTERNATELY REVERSIBLE MANNER

FIELD OF THE INVENTION

The invention relates to a dental preparation instrument, comprising a reversibly rotating tool that is, for example, used in the treatment of root canals. The preparation instrument has a drive for the tool.

BACKGROUND OF THE INVENTION

A rotating handpiece for endodontics is known from EP 1 196 109 B1, wherein a file is rotated such that it rotates across a first angular range in a first direction for cutting or smoothing, and rotates over a second angular range opposite the first direction to remove the abraded material, wherein the first angular range is greater than the second angular range and lies within a range of 90-180° and 45-120°, respectively.

It is known from EP 2 438 884 A1 that the angular range for cutting or smoothing is less than the elastic torsion angle of the tool, and that the angular range for cutting or smoothing is 3 to 20 times greater than the angular range for removal.

A motor is used in each case that has a reversible rotational direction and can be programmed by means of a control device. The disadvantage is that the handpiece requires a motor with special electronics, and the handpiece therefore cannot be used in existing dental workplaces with an existing motor control for a conventional, fully rotational motor.

The object of the invention is to avoid this disadvantage.

BRIEF SUMMARY OF THE INVENTION

A dental preparation instrument according to the invention works with a tool that rotates in an alternately reversible manner. A drive for the tool is provided. The drive provides a continuous, fully rotational motion. A gearing is arranged upstream from the tool in the drive train and converts the continuous, fully rotational motion of the drive into a rotating motion that is alternately reversible and is continuous when viewed over several reversals.

By means of the arrangement of the gearing in the preparation instrument, it is possible to connect the preparation instrument to conventional workplaces with a control for fully rotational motors. In particular, mechanical gearing is possible as the gearing.

In one advantageous further development, the gearing has a rotatably mounted input shaft and a rotatably mounted output shaft. A fixed gear wheel is arranged in the gearing. A mount is provided on the input shaft for a rotatable gear wheel that meshes with a fixed gear wheel and is rotatably mounted relative to the mount at a distance R from the middle axis of the fixed gear wheel. The rotatable gear wheel is connected to a sliding block at a distance from its rotary axis. The sliding block is guided in a sliding block guide connected to the output shaft.

In the interplay with the sliding block guide, the change in distance of the sliding block from the rotational center of the input or output shaft generates an alternating positive and negative direction of rotation which, by appropriately choosing the geometric relationships, causes a change in the direction of rotation of the output shaft.

Advantageously, the sliding block can be arranged on a lever extending away from the rotary axis of the rotatable gear wheel at a distance D that is either:
  greater than the radius r of the rotatable gear wheel and less than the radius R of the rotary axis of the rotatable gear wheel about the central axis of the fixed gear wheel, when the radius r of the rotatable gear wheel is less than the radius R of the rotary axis of the rotatable gear wheel about the central axis of the fixed gear wheel, or
  less than the radius r the rotatable gear wheel and greater than the radius R of the rotary axis of the rotatable gear wheel about the central axis of the fixed gear wheel, when the radius r of the rotatable gear wheel is greater than the radius R of the rotary axis of the rotatable gear wheel about the central axis of the fixed gear wheel.

Given these geometric relationships, a reversal of the direction of rotation can be ensured, wherein the corresponding elements of the two directions of rotation can be fixed by means of the geometric relationships.

Advantageously, the sliding block can be arranged on a lever extending away from the rotary axis of the rotatable gear wheel outside the circumference of the rotatable gear wheel. The lever is connected to the rotatable gear wheel. Consequently, establishment of the elements of the rotary angle is not dependent on the size of the gear wheel.

Advantageously, the sliding block can be arranged on the rotatable gear wheel within the circumference of the rotatable gear wheel. Additional components are thereby avoided.

Advantageously, the fixed gear wheel and rotatable gear wheel can be a spur gear such that the roll-off path of a point on the rotatable gear wheel is an epicycloid.

Advantageously, the fixed gear wheel can be a sun gear, and the rotatable gear wheel can be a spur gear such that the roll-off path of a point on the rotatable gear wheel is a hypocycloid.

Advantageously, an angle piece can be available to accommodate the tool, a motor can be available as the drive for the tool, and the gearing can be part of the angle piece, or part of the motor, or part of an additional connecting piece between the motor and angle piece.

BRIEF DESCRIPTION OF THE DRAWINGS

A device according to the invention is explained on the basis of the drawings. In the drawings.

DETAILED DESCRIPTION OF THE INVENTION

Figure 1:
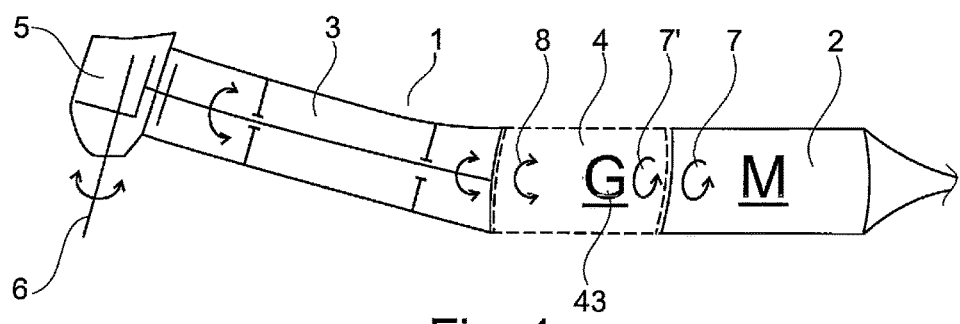
FIG. 1 shows a dental preparation instrument with a motor, an angle piece, and a connecting piece with gearing.

FIG. 1 schematically portrays a dental preparation instrument 1 comprising a drive in the form of a motor 2 and an angle piece 3, wherein a connecting piece 4 with a gearing 43 is placed between the motor 2 and the angle piece 3. The motor 2 is connected to a hose (not shown) through which supply lines are guided, for example, to ensure electrical supply to the motor, but also possibly to provide media such as light, water or air.

The angle piece 3 has a head 5 in which a tool 6 is rotatably mounted. The rotational motion of the motor 2 depicted by the arrow 7 is transmitted to the connecting piece 4 and is converted into an alternately reversing rotational motion designated by the double arrow 8 by the gearing G placed there which is also provided with reference number 43. This alternately reversing rotational motion is transmitted by the angle piece 3 to the tool 6.

Figure 2:
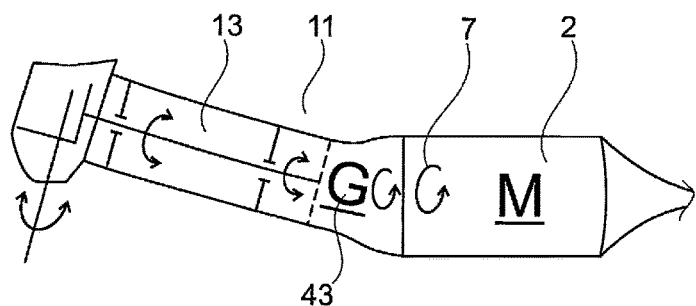
FIG. 2 shows a dental preparation instrument with a motor, an angle piece, and integrated gearing.

FIG. 2 shows a dental preparation instrument 11, wherein the gearing 43 is integrated in the angle piece such that, at the input to the angle piece 13, a fully rotational motion originating from a motor 2 can be received.

Figure 3:
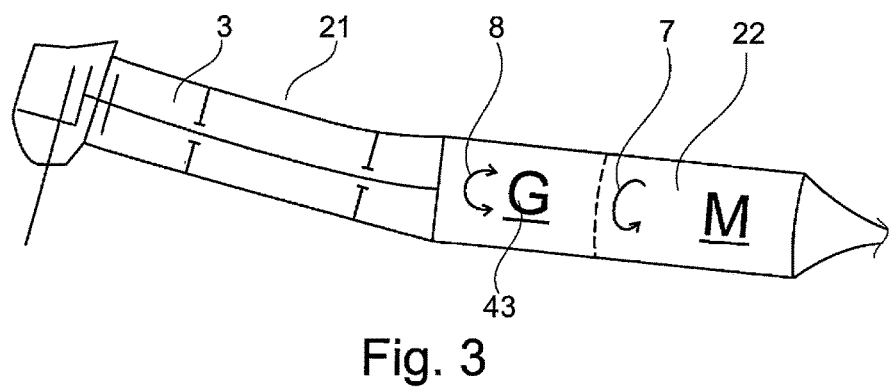
FIG. 3 shows a dental preparation instrument with a motor with integrated gearing and an angle piece.

FIG. 3 shows a dental preparation instrument 21, wherein the angle piece 3 from FIG. 1 can be connected to a motor 22 that is provided with a gearing which converts the fully rotational motion of the motor into an alternately reversing rotational motion depicted by the double arrow 8 and the arrow 7.

Figure 4:
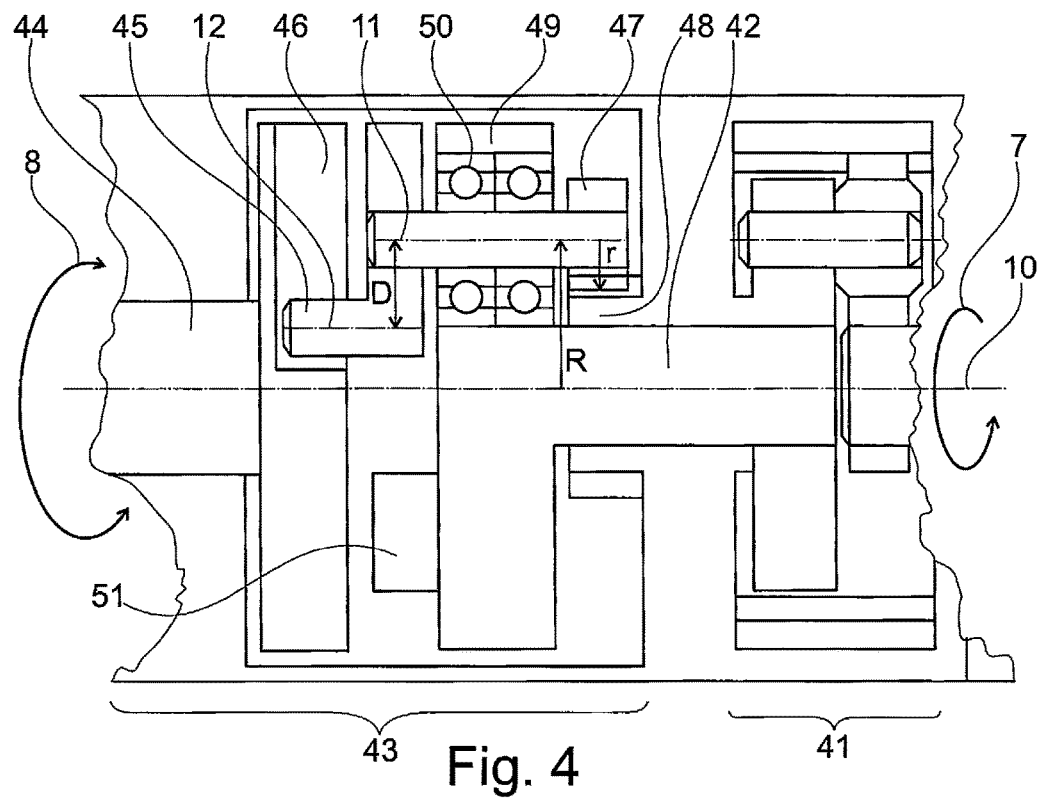
FIG. 4 shows a section through a gearing with a spur gear-spur gear toothing.

FIG. 4 shows a section through a gearing 43 with spur gear-spur gear toothing. The fully rotational motion about a central axis 10 provided by a motor (not shown) indicated by the arrow 7 is converted to a desired speed range by means of a reduction gear 41 such that there is a fully rotational motion about the central axis 10 by an input shaft 42 of the gearing 43. The gearing 43 has a rotatably mounted output shaft 44 which executes an alternately reversing rotational motion about the central axis 10 indicated by the arrow 8.

The fully rotational motion of the drive is converted into the alternately reversing rotational motion of the input shaft 44 by using a sliding block control in which a sliding block 45, executing a fully rotational motion, is guided in a sliding block guide 46 connected to the output shaft 44. The sliding block 45 is connected for conjoint rotation to a rotatable gear wheel 47 that is rotatably mounted and whose rotary axis 11 maintains a distance R to the central axis 10 of the input shaft 42 and engages with a fixed gear wheel 48 in a spur gear-spur gear connection between the gear wheels 47, 48, and wherein the fixed gear wheel 48 is placed inside, and wherein the rotatable gear wheel 47 rolls along the outer circumference of the fixed gear wheel 48.

The input shaft 42 has a mount 49 in which a bearing arrangement 50 is provided for rotatably bearing the rotatable gear wheel 47 about the rotary axis 11.

The sliding block 45 with its central axis 12 is situated at a distance D to the rotary axis 11 of the rotatable gear wheel 47, wherein the sliding block 45 is at an axial distance to the rotatable gear wheel 47 such that the rotatable gear wheel 47 is placed on one side of the mount 49, and the sliding block 45 is placed on the other side of the mount 49. To balance the weight of the sliding block 45, a counterweight 51 is provided on the mount 49. Instead of the counterweight 51, the sliding block control can be designed in duplicate and especially symmetrically in order to bring about a balance of weight.

Figure 5:
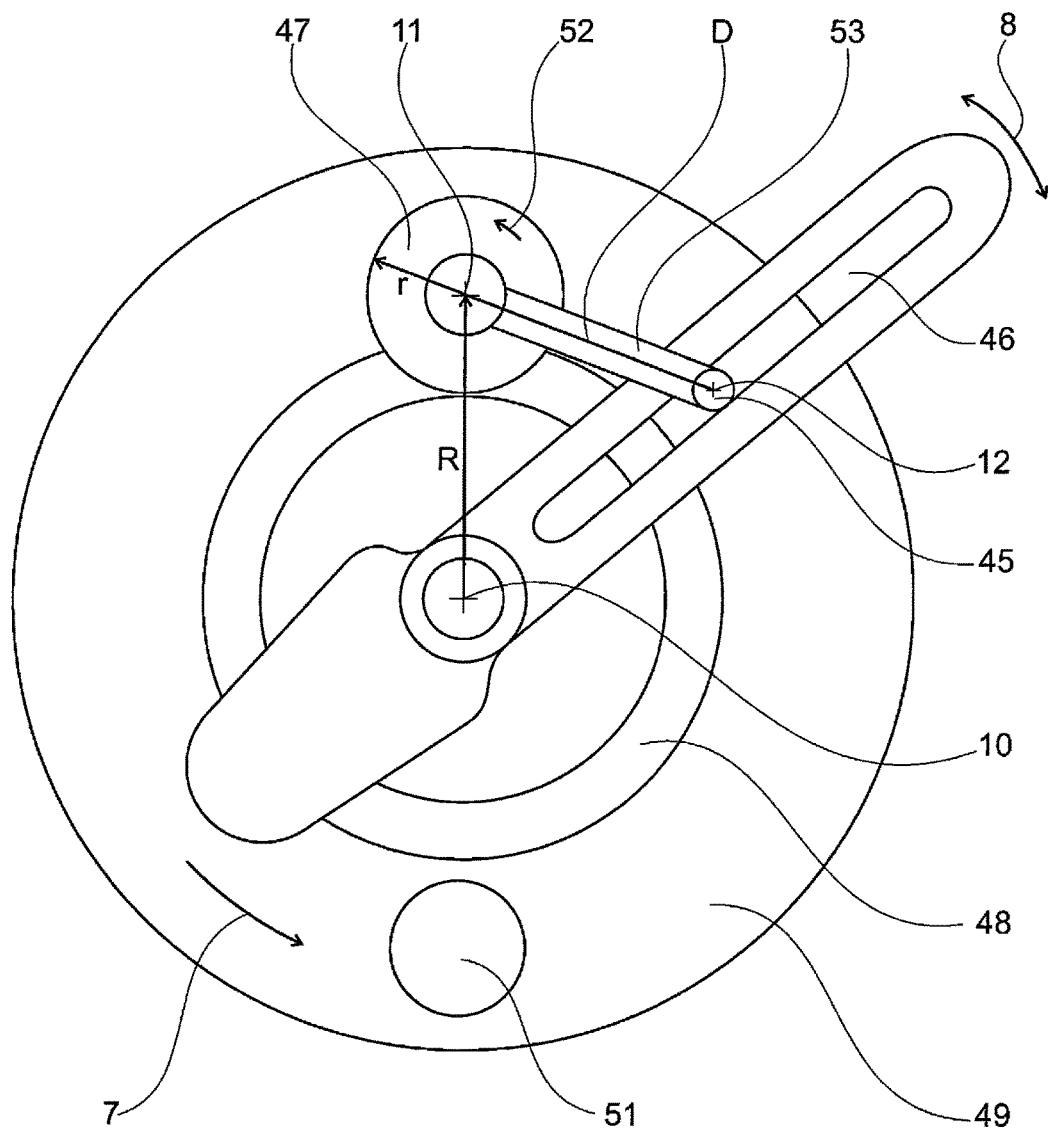
FIG. 5 shows a plan view of the gearing from FIG. 4.

FIG. 5 schematically illustrates the geometrical relationships. Proceeding from the mount 49 on which the counterweight 51 is placed at a distance from the central axis 10, the two gear wheels 47, 48 are depicted which are located behind the plane of the drawing and are actually covered by the mount 49. The rotatable gear wheel 47 supported in the mount 49 has a radius r and rotates about its rotary axis 11 which is situated at a distance R to the central axis 10, wherein it meshes with the fixed gear wheel 48 and rolls thereupon when the mount 49 rotates in the direction of the arrow 7.

Together with the rotatable gear wheel 47, the sliding block 45, which is situated on the rotatable gear wheel 47 at a distance D to the rotary axis 11 of the rotatable gear wheel 47, also rotates via a lever 53 which is indicated by the arrow of 52 on the rotatable gear wheel 47. During this, the sliding block is located outside of the circumference of the rotatable gear wheel 47. Since the sliding block 45 is guided in a longitudinally displaceable and rotatable manner in a sliding block guide 46 connected to the output shaft (not shown), the sliding block guide 46 follows the rotational motion of the sliding block 45 about the rotary axis 11 placed eccentric to the central axis 10, and in so doing moves about the central axis 10, indicated by the arrow 8.

The distance D of the sliding block to the rotary axis 11 of the rotatable gear wheel 47 in the depicted case is greater than the radius r of the rotatable gear wheel 47 and less than the radius R of the rotary axis 11 of the rotatable mounted gear wheel 47 about the central axis 10 of the fixed gear wheel 48, since the radius r of the rotatable gear wheel 47 is less than the radius R of the rotary axis 11 of the rotatable gear wheel 47 about the central axis 10 of the fixed gear wheel 48.

Figure 6:
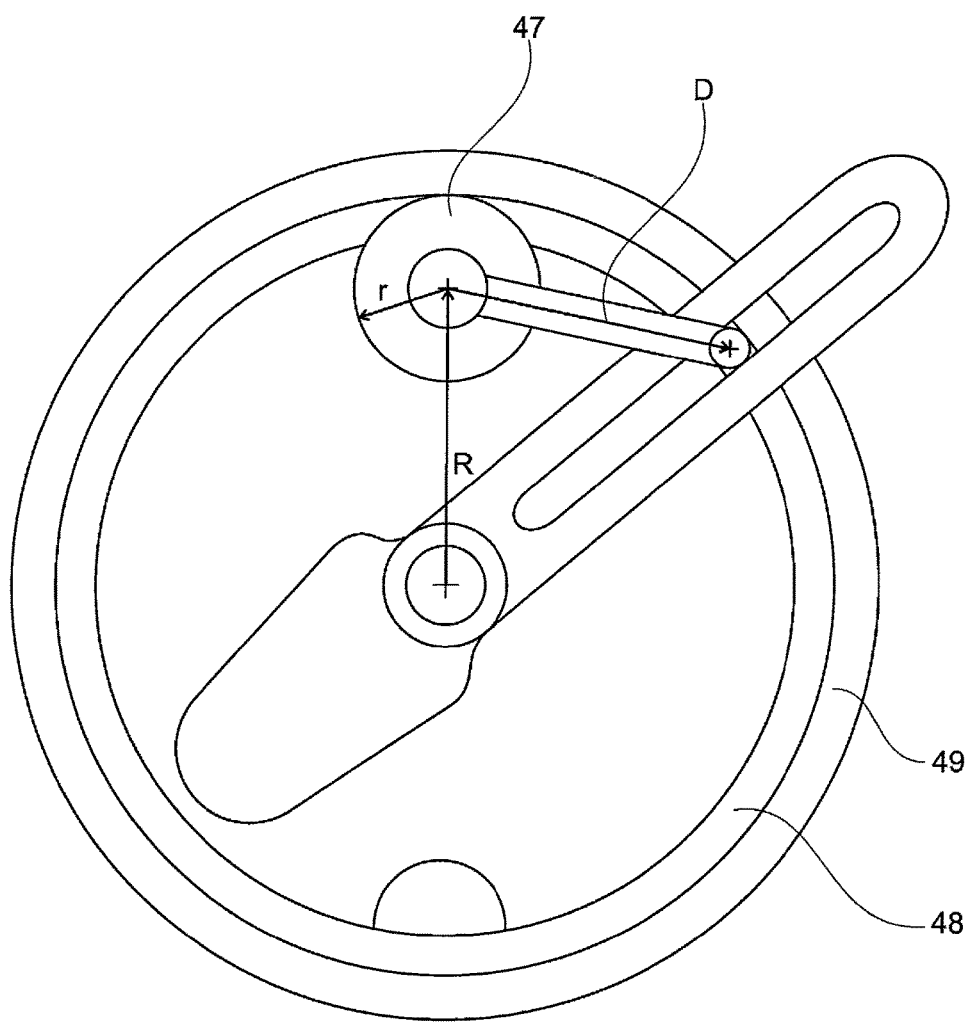
FIG. 6 shows a plan view of a gearing with a sun gear-spur gear toothing.

FIG. 6 shows that a sun gear-spur gear-toothing of the fixed gear wheel 48 with the rotatable gear wheel 47 can be provided instead of the spur gear-spur gear toothing. This does not alter any of the kinematics of the motion, however.

Figure 7:
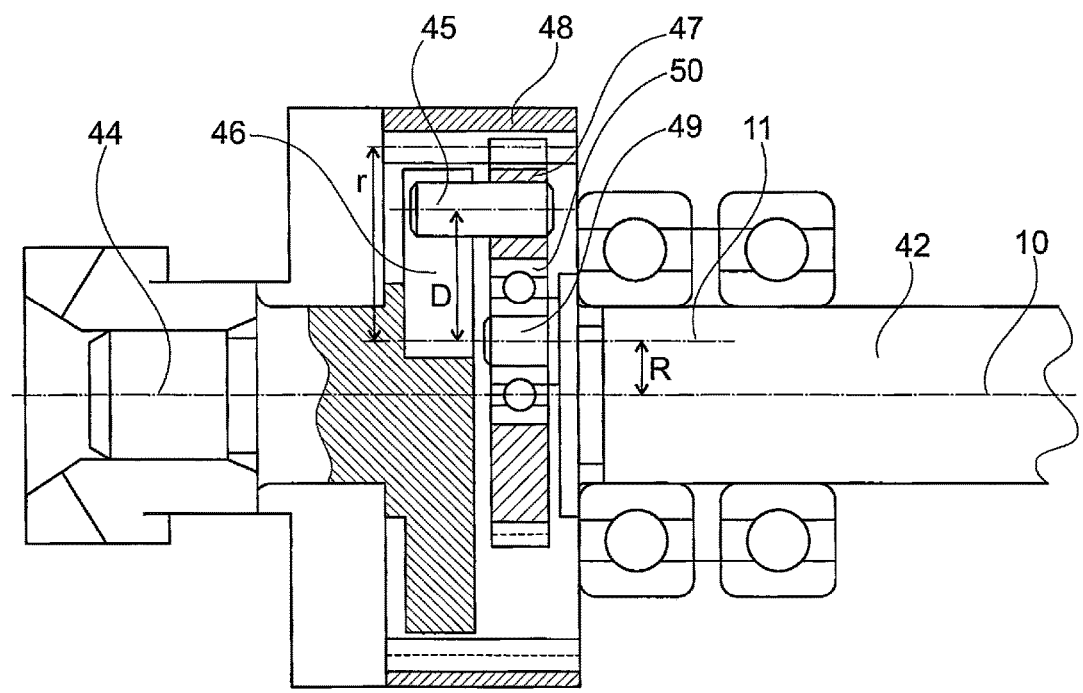
FIG. 7 shows a longitudinal section of another gearing with a sun gear-spur gear toothing.

FIG. 7 shows a structural design of an alternative sun gear-spur gear toothing which is more compact in regard to the structural length. The fixed gear wheel 48 surrounds the rotatable gear wheel 47 which is supported on a mount 49 of the input shaft 42 by means of a bearing 50, and its rotary axis 11 lies at a distance R to the central axis 10 of the input shaft 42. The sliding block 45 is attached to the rotatable gear wheel 47 at a distance D to the rotary axis 11 and engages in the sliding block guide 46 connected to the output shaft 44. The sliding block 45 is situated on the rotatable gear wheel 47 within the circumference of the rotatable gear wheel 47.

In this case, the distance D of the sliding block 45 to the rotary axis 11 of the rotatable gear wheel 47 is less than the radius r of the rotatable gear wheel 47, and greater than the radius R of the rotary axis 11 of the rotatable gear wheel 47 about the central axis 10 of the fixed gear wheel 48. The radius r of the rotatable gear wheel 47 is then larger than the radius R of the rotary axis 11 of the rotatable gear wheel 47 around the central axis 10 of the fixed gear wheel 48.

Figure 8:
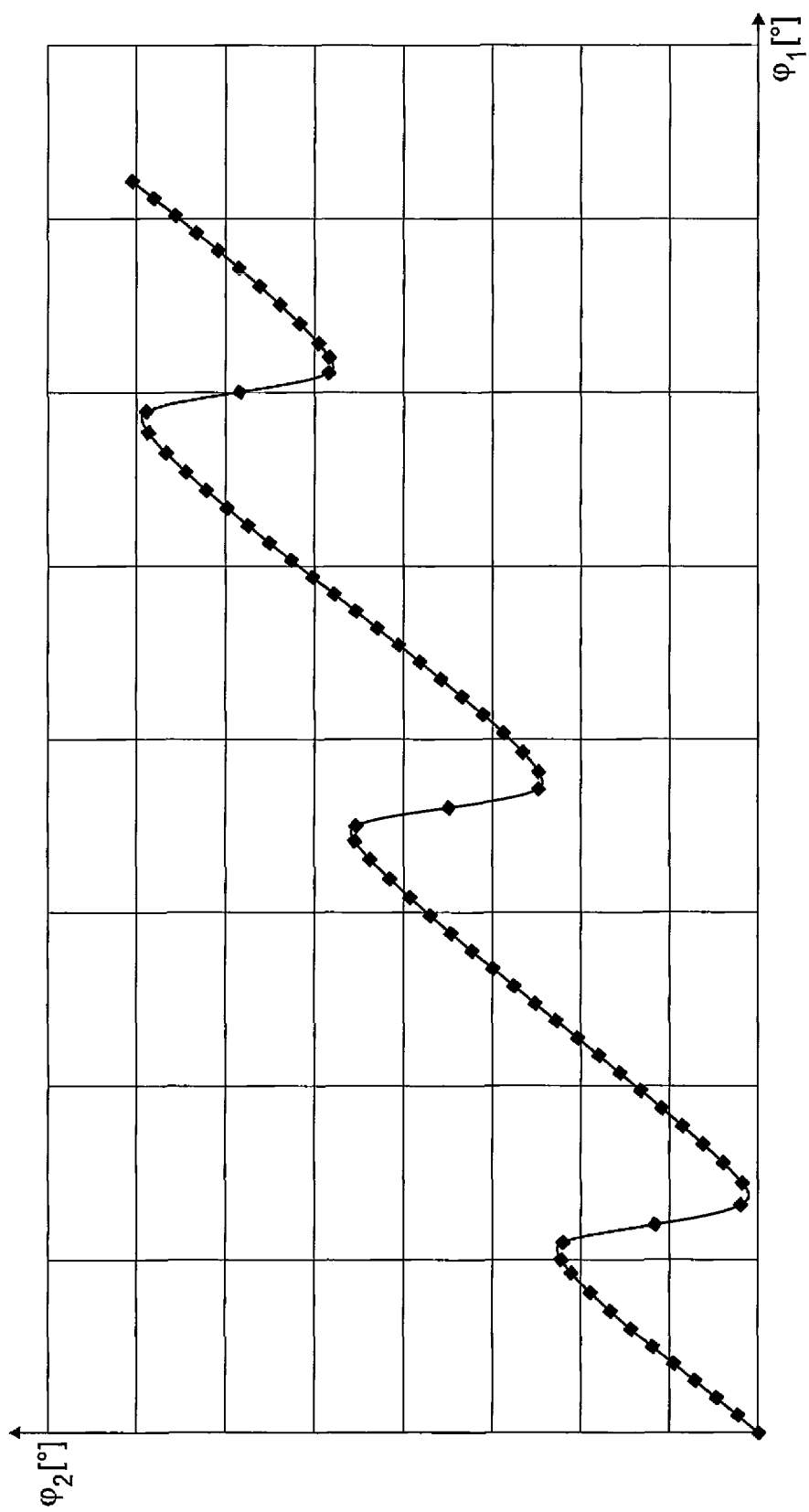
FIG. 8 shows a schematic path of the rotary angle at the output over the rotary angle on the drive.

FIG. 8 shows a schematic path of the rotary angle Phi2 at the output over the rotary angle Phi1 on the drive. It can be seen that the continuous, fully rotational motion of the drive is converted into an alternately reversing rotational motion of the output which is continuous as viewed over several reversals and therefore progresses as viewed collectively.

Given a corresponding design of the gear wheels 47, 48, a transmission ratio can also be achieved between the drive and output if this is desired.

In principle, friction wheels can be used in the gearing instead of toothed wheels in order to provide the gearing function.

The invention claimed is:
1. A dental preparation instrument, comprising:
a motor configured to provide a continuous rotational motion;

a gearing configured to convert the continuous rotational motion of the motor into a rotating motion that is alternately reversible and continuous when viewed over several reversals;
wherein the gearing includes:
a rotatably mounted input shaft,
a rotatably mounted output shaft,
a fixed gear wheel, and
a mount provided on the rotatably mounted input shaft for a rotatable gear wheel arranged to mesh the fixed gear wheel,
wherein the rotatable gear wheel is rotatably mounted relative to the mount at a distance R from a central axis of the fixed gear wheel,
wherein a sliding block connected to the rotatable gear wheel is at a distance D from a rotary axis of the rotatable gear wheel, and
wherein the sliding block is guided in a sliding block guide connected to the rotatably mounted output shaft;
wherein the distance D is either;
   (i) greater than a radius r of the rotating gear wheel and smaller than a radius R of the rotary axis of the rotating gear wheel about a central axis of the fixed gear wheel, when the radius r of the rotating gear wheel is less than the radius R of the rotary axis of the rotating gear wheel about the central axis of the fixed gear wheel, or
   (ii) smaller than the radius r of the rotating gear wheel and greater than the radius R of the rotary axis of the rotating gear wheel about the central axis of the fixed gear wheel, when the radius r of the rotating gear wheel is greater than the radius R of the rotary axis of the rotating gear wheel about the central axis of the fixed gear wheel;
wherein the sliding block is situated on a lever extending away from the rotary axis of the rotatable gear wheel outside of the circumference of the rotatable gear wheel, and
wherein the lever is connected to the rotatable gear wheel.

2. The dental preparation instrument according to claim 1, wherein the sliding block is disposed on the rotatable gear wheel within a circumference of the rotatable gear wheel.

3. The dental preparation instrument according to claim 1, wherein the fixed gear wheel and the rotatable gear wheel form a spur gear such that a roll-off path of a point on the rotatable mounted gear wheel is an epicycloid.

4. The dental preparation instrument according to claim 1, wherein the fixed gear wheel is a sun wheel, and the rotatable gear wheel is a spur gear such that a roll-off path of a point on the rotatably mounted gear wheel is a hypocycloid.

5. The dental preparation instrument according to claim 1, further comprising:
   an angle piece configured to is available to accommodate the motor.

6. The dental preparation instrument according to claim 5, wherein the gearing is located within one of: the angle piece, the motor, or a connecting piece between the angle piece and the motor.

7. The dental preparation instrument according to claim 6, further comprising: a tool connected to the gearing and configured to rotate in an alternately reversible manner in accordance with the rotating motion of the gearing.

* * * * *